United States Patent [19]

Alaimo et al.

[11] 4,225,526
[45] Sep. 30, 1980

[54] 8-[(4-AMINOPHENYL)SULFONYL]AMINO-2-NAPHTHALENYL PHOSPHORODIAMIDATE

[75] Inventors: Robert J. Alaimo; Ozra E. Millner, Jr., both of Norwich, N.Y.

[73] Assignee: Morton-Norwich Products, Inc., Norwich, N.Y.

[21] Appl. No.: 63,127

[22] Filed: Aug. 3, 1979

[51] Int. Cl.$^2$ ............................................. C07C 143/82
[52] U.S. Cl. ............................. 260/397.7 R; 424/198; 424/228
[58] Field of Search .................................. 260/397.7 R

[56] References Cited

U.S. PATENT DOCUMENTS 2,245,539  6/1941  Warnat ........................ 260/397.7 R
4,032,601  6/1977  Birum ......................... 260/397.7 R

OTHER PUBLICATIONS

Northey, The Sulfonamides and Allied Compounds, Frontispage, and pp. 49, 58–60 and 147, Reinhold Publishing Corp. NY (1948).

Primary Examiner—John D. Randdolph
Attorney, Agent, or Firm—Anthony J. Franze

[57] ABSTRACT

8-[(4-Aminophenyl)sulfonyl]amino-2-napthalenyl phosphorodiamidate is useful as an inhibitor of the enzyme urease.

1 Claim, No Drawings

8-[(4-AMINOPHENYL)SULFONYL]AMINO-2-NAPHTHALENYL PHOSPHORODIAMIDATE

This invention is concerned with chemical compounds. More particularly, it is concerned with 8-[(4-aminophenyl)sulfonyl]amino-2-naphthalenyl phosphorodiamidate.

This compound is a potent inhibitor of the enzyme urease. Urease is produced by a number of bacterial species particularly Proteus exemplary of which are *Proteus mirabilis, Proteus vulgaris, Proteus morganii* and *Proteus rettgeri*, all of which are well-known urinary tract pathogens. Their ability to produce urease in the urinary tract, which contains substantial amounts of urea, provides a setting wherein urease splits urea according to this scheme:

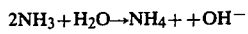

This reaction sequence poses a hyperammonuria and alkalinity of the urine affording a locale favorable to the formation of struvite ($MgNH_4PO_4.6H_2O$) a predominant component of infected urinary calculi. Such struvite formation and alkalinization of the urine render the treatment of urinary tract infections difficult and oftentimes recalcitrant to otherwise effective urinary tract antiseptics.

The compound of this invention is highly effective in inhibiting urease which is intimately associated with the pathogenicity of the Proteus species of bacteria. Thus, a concentration of this compound in the amount of $4 \times 10^{-7}$ molar evinces a 50% inhibition of the urease of intact *Proteus mirabilis* cells.

The anti-urease potency of the compound of this invention was determined using intact *Proteus mirabilis* cells as the source of urease. Compounds were preincubated with *Proteus mirabilis* cells suspended in a saline solution (0.1 molar) buffered with 0.1 molar tris(hydroxymethyl)aminomethane (pH 8.0). After 40 minutes preincubation, the remaining urease activity was determined by collecting the ammonia formed in five minutes after the addition of the substrate, urea. Ammonia assays were carried out according to the procedure of Seligson and Seligson [J. Lab. Clin. Med. 38, 324–330 (1951)]. Percent inhibition was calculated by comparing the amount of ammonia generated by cells preincubated with 8-[(4-aminophenyl)sulfonyl]amino-2-naphthalenyl phosphorodiamidate with the controls in which preincubation was carried out in the absence of compound.

In order that this invention may be fully available to and understood by those skilled in the art, the following procedure is supplied:

A. 8-[(4-Nitrophenyl)sulfonyl]amino-2-naphthol

A mixture of 8-amino-2-hydroxynapthalene (50 g, 0.3 mole) and 4-nitrobenzenesulfonyl chloride (55 g, 0.25 mole) in pyridine (500 ml) was heated under reflux for 2.5 hours then allowed to stand O/N. The mixture was poured in ice water and acidified with HOAc. The precipitated product was boiled in hexane and then recrystallized from ethyl acetate-hexane to give 40 g of green product (47%). This material was used in Part B.

B. 8-[(4-Nitrophenyl)sulfonyl]amino-2-naphthalenyl Phosphorodiamidate

8-[(4-Nitrophenyl)sulfonyl]amino-2-naphthol (30 g, 0.09 mole) and $ALCL_3$ (1 g) was suspended in $POCl_3$ (350 ml). The mixture was heated under reflux for four hours. The excess $POCl_3$ was removed in vacuo and the residue flushed two times with chloroform. The residue was suspended in $CHCl_3$ (400 ml) and the stirred mixture was saturated with $NH_3$ for about 30 minutes at $-10°$. After the addition, the mixture was stirred at room temperature then filtered. The product was washed with $CHCl_3$, then ether. The solid was suspended in $H_2O$ and acidified with acetic acid. The crude product weighed 41 g (100%). Recrystallization from $CH_3NO_2$ dimethylformamide provided analytical material which melted at $234°-235°$.

Anal. Calcd. for $C_{16}H_{15}N_4O_6SP$: C, 45.50; H, 3.58; N, 13.27. Found: C, 45.68; H, 3.60; N, 13.33.

The product was used in Part C.

C. 8-[(4-Aminophenyl)sulfonyl]amino-2-naphthalenyl Phosphorodiamidate

To 7 g (0.017 mole) of nitro compound from Part B was added 300 ml of methanol and Pd/C catalyst. The mixture was hydrogenated at 35 psi. After the reduction was complete, the mixture was heated and filtered. The product was precipitated by addition of $H_2O$. The crude product was recrystallized from isopropanol gave 4 g of product (60%). Analytical material was obtained by additional recrystallization from isopropanol (Darco) m.p. $209°-210°$.

Anal. Calcd. for $C_{16}H_{17}N_4O_4SP$: C, 48.98; H, 4.37; N, 14.28. Found: C, 48.58; H, 4.30; N, 14.03.

What is claimed is:
1. The compound 8-[(4-Aminophenyl)sulfonyl]amino-2-naphthalenyl phosphorodiamidate.